US00RE33956E

United States Patent [19]

Lin et al.

[11] E Patent Number: Re. 33,956

[45] Reissued Date of Patent: Jun. 9, 1992

[54] INSPECTION SYSTEM FOR ARRAY OF MICROCIRCUIT DIES HAVING REDUNDANT CIRCUIT PATTERNS

[75] Inventors: Lawrence H. Lin, Alamo; Daniel L. Cavan, Woodside; Robert B. Howe, San Jose, all of Calif.

[73] Assignee: Insystems, Inc., San Jose, Calif.

[21] Appl. No.: 613,208

[22] Filed: Nov. 14, 1990

Related U.S. Patent Documents

Reissue of:

[64] Patent No.: 4,806,774
Issued: Feb. 21, 1989
Appl. No.: 60,090
Filed: Jun. 8, 1987

[51] Int. Cl.[5] ..... G02B 27/42

[52] U.S. Cl. ..... 250/550; 250/572; 382/31; 356/237; 356/354

[58] Field of Search ..... 250/562, 563, 550, 572, 250/548; 356/392, 394, 354, 237; 382/31

[56] References Cited

U.S. PATENT DOCUMENTS

| | | | |
|---|---|---|---|
| 3,614,232 | 10/1971 | Mathisen | 356/394 |
| 4,000,949 | 1/1977 | Watkins | 356/392 |
| 4,253,564 | 10/1982 | Roach | 250/550 |
| 4,282,510 | 8/1981 | Southgate | 250/550 |
| 4,330,775 | 5/1982 | Iwamoto et al. | 382/31 |
| 4,370,024 | 1/1983 | Task et al. | 250/550 |

FOREIGN PATENT DOCUMENTS

| | | |
|---|---|---|
| 0017371 | 10/1980 | European Pat. Off. . |
| 0214436 | 3/1987 | European Pat. Off. . |

OTHER PUBLICATIONS

Kahn, Frederic J., "Large Area, Engineering Drawing Quality Displays Using Laser Addressed Smectic Liquid Crystal Light Valves," Automation Technology Instutte Conference, Montreal, Canada, Feb. 1987.

W. M. Sterling et al., "Reticle Inspection Using Diffraction Pattern Making," Xerox Disclosure Journal, vol. 9, No. 1, Jan./Feb. 1984, pp. 65–66.

E. Ochoa et al., "Real-time enhancements of defects in a periodic mask using photorefractive $Bi_{12}SiO_{20}$," Optics Letters, vol. 10, No. 9, Sep. 1985, pp. 430–432.

*Primary Examiner*—David C. Nelms

*Attorney, Agent, or Firm*—Stoel Rives Boley Jones & Grey

[57] ABSTRACT

An inspection system (10, 100) employs a Fourier transform lens (34, 120) and an inverse Fourier transform lens (54, 142) positioned along an optic axis (48, 144) to produce from an illuminated area of a patterned specimen wafer (12) a spatial frequency spectrum whose frequency components can be selectively filtered to produce an image pattern of defects in the illuminated area of the wafer. Depending on the optical component configuration of the inspection system, the filtering can be accomplished by a spatial filter of either the transmissive (50) or reflective (102) type. The lenses collect light diffracted by a wafer die (14) aligned with the optic axis and light diffracted by other wafer dies proximately located to such die. The inspection system is useful for inspecting only dies having many redundant circuit patterns. The filtered image strikes the surface of a two-dimensional photodetector array (58) which detects the presence of light corresponding to defects in only the illuminated on-axis wafer die. Inspection of all possible defects in the portions of the wafer surface having many redundant circuit patterns is accomplished by mounting the wafer onto a two-dimensional translation stage and moving the stage (40) so that the illuminated area continuously scans across the wafer surface from die to die until the desired portions of the wafer surface have been illuminated. The use of a time delay integration technique permits continuous stage movement and inspection of the wafer surface in a raster scan fashion.

58 Claims, 6 Drawing Sheets

250
254
254
254
X
Y
280
280
280
304
302
254
282
278
284a
284b
274b
274c
274a
286
276
264
284a
254
280
280
282
302
296d
254
274b
274a
278
296
262
286
296c
296b
296a
276
300
294
268
274a
260
298
290a
290b
290c
272
290d
270
264
274b
284a
290
264
266
288
292
X
Y

INSPECTION SYSTEM FOR ARRAY OF MICROCIRCUIT DIES HAVING REDUNDANT CIRCUIT PATTERNS

Matter enclosed in heavy brackets [ ] appears in the original patent but forms no part of this reissue specification; matter printed in italics indicates the additions made by reissue.

TECHNICAL FIELD

The present invention relates to inspection systems for use in the manufacture of microcircuits and, in particular, to a real-time defect inspection system for use in the manufacture of microcircuits of the type that includes an array of dies each having many redundant circuit patterns.

BACKGROUND OF THE INVENTION

Two exemplary and very similar inspection systems for pattern defects in photomasks employed in the large-scale manufacture of semiconductor devices and integrated circuits are described in U.S. Pat. Nos. 4,000,949 of Watkins and 3,614,232 of Mathisen. The systems of Watkins and Mathisen contemplate the simultaneous inspection of all of the dies on a photomask which contains a regular array of normally identical dies to detect the presence of nonperiodic defects, i.e., defects in one die not identically repeated in the remaining dies of the array.

This task is accomplished by illuminating simultaneously all of the dies of a specimen photomask with collimated coherent light emanating from a laser to develop a composite diffraction pattern whose spatial distribution is the combination of two components. The first component is the interference pattern of the array of dies, and the second component is the interference pattern of a single die of the array. The first and second components are sometimes called an inter-die interference pattern and an intra-die interference pattern, respectively. The light transmitted by the photomask strikes a double-convex lens which distributes the light on a spatial filter positioned a distance equal to one focal length behind the lens.

The spatial filter comprises a two-dimensional Fourier transform pattern of a known error-free reference photomask against which the specimen photomask is compared. The filter is opaque in the areas corresponding to spatial frequency components of the error-free Fourier transform pattern and is transparent in areas not included in the error-free Fourier transform pattern. Neither the Watkins patent nor the Mathisen patent specifies the design parameters of the lens. The Mathisen patent states only that the lens is of suitable numerical aperture and magnification power to cover the area of the specimen photomask.

The spatial frequency components corresponding to the defects in the specimen photomask are largely transmitted through the spatial filter and can be processed in either one of two ways. In the Watkins system, the light transmitted through the spatial filter strikes another double-convex lens that is properly positioned to define an image of the specimen photomask, absent any information blocked by the spatial filter. The imaging light not blocked by the spatial filter appears in locations that represent the position in the specimen photomask where defects are present. In the Mathisen system, the light transmitted through the spatial filter is sensed by a photodetector that produces an output signal which activates a "no-go" alarm.

The Watkins and Mathisen patents imply that systems of the type they describe require both inter- and intra-die interference pattern information to determine the presence of defects in the specimen pattern. The inter-die interference pattern information is of particular concern because it consists of very closely spaced light spots that are extremely difficult to resolve by a Fourier transform lens. The realization of such a lens is further complicated for inspection systems that use an inverse Fourier transform lens to form an image of the specimen pattern from the Fourier transform light pattern. The reason is that the design of each of the lenses is compromised to accomplish an overall system design that accomplishes both the Fourier transform pattern and image forming functions. It is, therefore, exceedingly difficult to obtain from such a system design the resolution required to acquire inter-die interference pattern information. The above lens design problem is encountered in systems of the type that simultaneously inspects the entire area of each of the dies of a specimen photomask array and, as a consequence, renders such systems unreliable and impracticable for commercial use.

SUMMARY OF THE INVENTION

An object of the present invention is, therefore, to provide a reliable defect inspection system for use in the manufacture of microcircuits.

Another object of this invention is to provide such a system that applies the techniques of Fourier optics but does not contemplate the use of inter-die interference pattern information to determine the presence of defects in the manufacture of microcircuits of the type that comprises an array of normally identical dies.

A further object of this invention is to provide such a system that is capable of developing from a microcircuit pattern an essentially aberration-free Fourier transform light pattern from which an accurate image corresponding to defects in the microcircuit pattern can be formed.

Still another object of this invention is to provide an inspection method that uses intra-die interference pattern information to determine the presence of defects in a microcircuit array pattern of normally identical dies.

The present invention relates to a method and system for use in the manufacture of microcircuits and is described herein by way of example only with reference to a real-time inspection system for defects in surfaces of semiconductor wafers of the type that includes an array of circuit dies of which each has many redundant circuit patterns. Such semiconductor wafers include, for example, random access and read only memory devices and digital multipliers.

Two preferred embodiments of the inspection system employ a Fourier transform lens and an inverse Fourier transform lens positioned along an optic axis to produce from an illuminated area of a patterned specimen wafer a spatial frequency spectrum whose frequency components can be selectively filtered to produce an image patter of defects in the illuminated area of the wafer. The lenses collect light diffracted by a wafer die aligned with the optic axis and light diffracted by other wafer dies proximally located to such die, rather than light diffracted by the entire wafer. This restriction limits the applicability of the inspection system to dies having many redundant circuit patterns but permits the use of lenses that introduce off-axis aberrations that would otherwise alter the character of the Fourier transform pattern and the filtered defect image.

Such lenses are relatively easy to manufacture because the redundant circuit patterns typically repeat at 50 micron intervals and thereby produce spatial frequency components spaced apart by a distance of about 1.0 millimeter, which is resolvable by conventional optical components. The Fourier transform and imaging areas are preferably of sufficient sizes to accommodate light from only the wafer die aligned with the optic axis. The spatial filter blocks the spatial frequencies of the error-free Fourier transform of such die, i.e., the spatial filter contains only intra-die interference pattern information.

The wafer is positioned in the front focal plane of the Fourier transform lens, and the patterned surface of the wafer is illuminated by a collimated laser beam. The Fourier transform pattern of the illuminated wafer surface is formed in the back focal plane of the Fourier transform lens. A previously fabricated spatial filter is positioned in the plane of the Fourier transform pattern and effectively stops the light transmission from the redundant circuit patterns of the illuminated dies of the wafer but allows the passage of light originating from possible defects.

The inverse Fourier transform lens receives the light either transmitted through or reflected by the spatial filter and performs the inverse Fourier transform on the filtered light diffracted by the illuminated wafer area. Whether the spatial filter is of a type that transmits or reflects light depends on the embodiment of inspection system in which it is incorporated. The filtered image strikes the surface of a two-dimensional photodetector array which detects the presence of light corresponding to defects in only the illuminated on-axis wafer die. The photodetector array is centrally positioned about the optic axis and has a light-sensitive surface area of insufficient size to cover the image plane area in which the defect image corresponding to the on-axis die appears. The inspection of all possible defects in the portions of the wafer surface having many redundant circuit patterns is accomplished by mounting the wafer onto a two-dimensional translation stage and moving the stage so that the illumination area defined by the laser beam continuously scans across the wafer surface from die to die until the desired portions of the wafer surface have been illuminated. The use of a time delay integration technique permits continuous stage movement and inspection of the portions of the wafer surface having many redundant circuit patterns in a stripe-to-stripe raster scan fashion.

The present invention is advantageous because the spatial filter need not be fabricated with the use of an error-free specimen wafer. The reason is that any defects present in such a wafer would produce light of insufficient intensity to expose the spatial filter recording medium.

The present invention detects defects in a specimen pattern by using only intra-die information corresponding to areas of the specimen pattern having many redundant circuit patterns. The premises underlying the inspection method of the present invention are that inter-die interference pattern information is unnecessary if only areas of many redundant patterns are inspected and that inspection of only such areas provides sufficient statistical sampling to determine the defect distribution for the entire specimen pattern.

Additional objects and advantages of the present invention will be apparent from the following detailed description of preferred embodiments thereof, which proceeds with reference to the accompanying drawings.

DETAILED DESCRIPTION OF PREFERRED EMBODIMENTS

Figure 1:
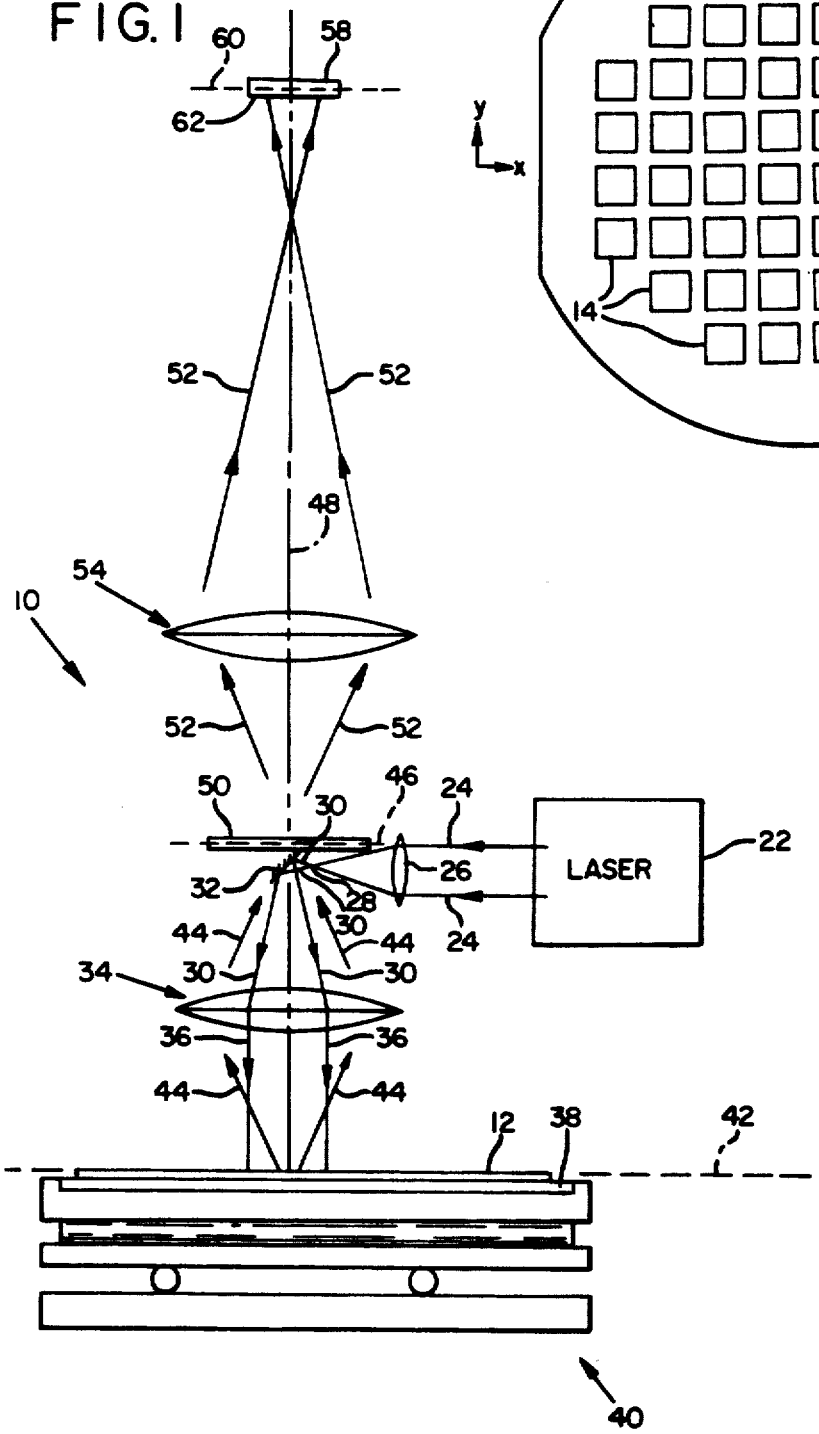
FIG. 1 is a schematic diagram of the optical components of a first preferred embodiment of the defect inspection system of the present invention.
Figure 2:
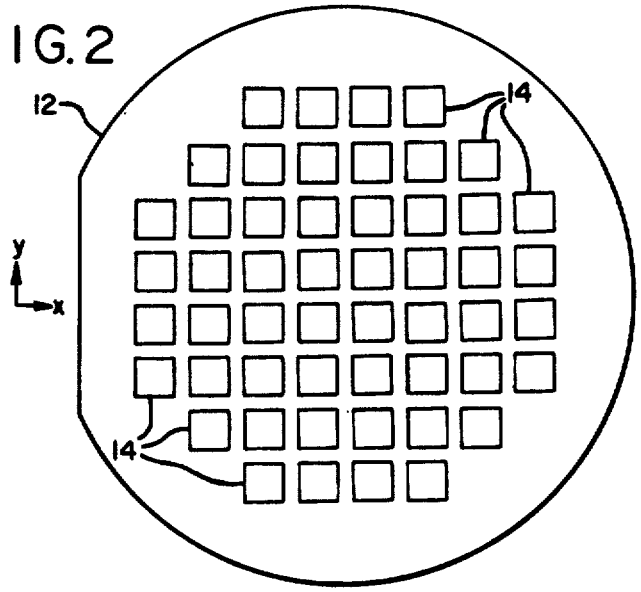
FIG. 2 is a diagram of a semiconductor wafer comprising a regular array of normally identical dies of the type suitable for defect inspection by the systems of FIGS. 1 and 6.
Figure 3A:
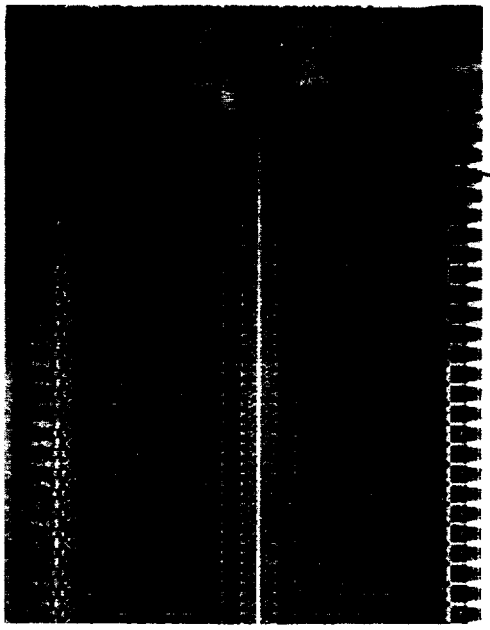
FIGS. 3A–3C are photographs of an exemplary single die of the semiconductor wafer of FIG. 2 showing within such die a highly redundant circuit pattern for consecutively increasing magnifications.
Figure 3B:
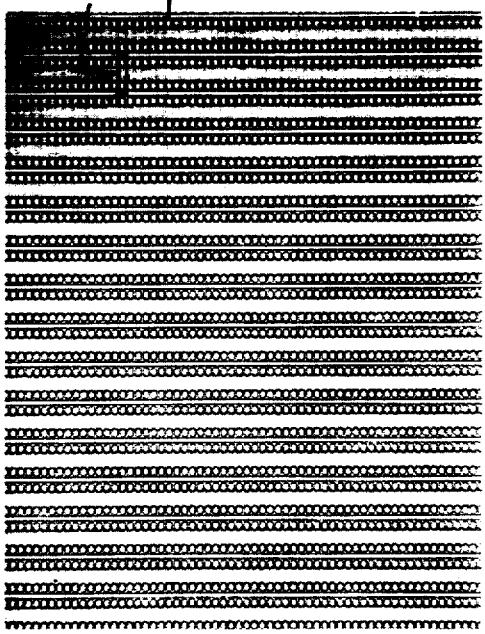
Figure 3C:
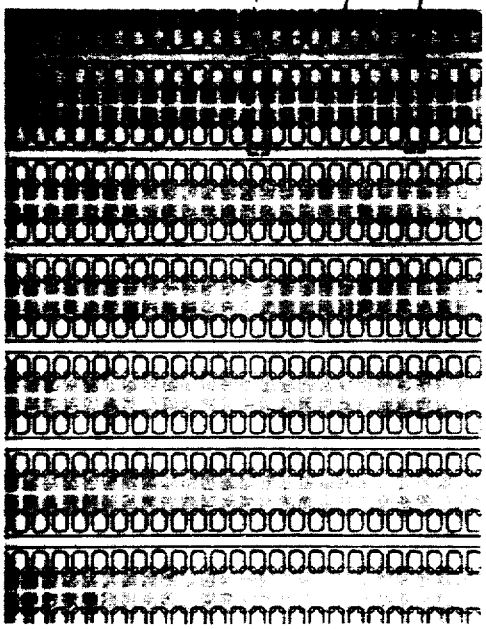

FIG. 1 is a schematic diagram of a first preferred embodiment of an inspection system 10 of the present invention that is designed to detect semiconductor wafer defects having a diameter of about one-quarter micron or larger in the presence of a periodic structure comprising many redundant circuit patterns. FIG. 2 is a diagram of a semiconductor wafer 12 of the type inspection system 10 is designed to inspect for defects. Wafer 12 includes a regular array of normally identical dies 14 of which each has at least about twenty redundant circuit patterns 16 along each of the X-axis 18 and Y-axis 20. Each die 14 is typically of square shape with about 3 millimeter sides. FIGS. 3A–3C are photographs of an exemplary single die 14 showing highly repetitive circuit pattern within such element for consecutively increasing magnifications. Although they are of rectangular shape as shown in FIGS. 3A–3C, circuit patterns 16 are assumed for purposes of simplifying the following discussion to be of square shape with about 50 micron sides.

With reference to FIG. 1, inspection system 10 includes a laser source 22 that provides a nearly collimated beam of 442.5 nanometer monochromatic light rays 24 that strike a lens 26 that converges the light rays to a point 28 located in the back focal plane of lens 26. The light rays 30 diverging from focal point 28 strike a small mirror 32 that is positioned a short distance from focal point 28 to reflect a relatively narrow circular beam of light toward a Fourier transform lens section 34, which is shown in FIG. 1 as a single element but which is implemented in five lens elements as will be further described below. Mirror 32 obscures a small region in the center of the Fourier transform plane defined by lens section 34. The size of the obscured region is sufficiently small so that defect information, which is located everywhere in the Fourier transform plane, is only insignificantly blocked by mirror 32.

The effective center of Fourier transform lens section 34 is positioned a distance of slightly less than one focal length away from mirror 32 to provide collimated light rays 36 that strike the patterned surface of wafer 12. Wafer 12 is mounted in a chuck 38 that constitutes part of a two-dimensional translation stage 40. Wafer 12 is positioned in the object or front focal plane 42 of lens section 34, and the collimated light rays 36 illuminate the patterned surface of wafer 12. The collimated light rays 36 illuminate a 20 millimeter diameter area of the surface of wafer 12. The light rays 44 diffracted by the illuminated area of wafer 12 pass through lens section 34 and form the Fourier transform pattern of the illuminated wafer surface in the back focal plane 46 of lens section 34.

The Fourier transform pattern comprises an array of bright spots of light that are distributed in back focal plane 46 in a predictable manner. The 20 millimeter diameter illuminated area of wafer 12 provides a Fourier transform pattern of sufficient accuracy because it is formed from many redundant circuit patterns. The design of lens section 34 is, however, such that it has only a 3 millimeter object field diameter to form in the image plane 60 an essentially aberration-free image of defects in the semiconductor wafer. An entire die can be inspected for defects because translation stage 40 moves the die through the illuminated area. Therefore, a relatively large area of wafer 12 is illuminated to develop an accurate Fourier transform pattern of the redundant circuit patterns, but [a] *an inverse Fourier transform* lens *section 54* of relatively small object field diameter collects the light diffracted by *the central portion of* the illuminated area to minimize the introduction of aberrations into the [Fourier transform pattern] *image* as it is formed.

A previously fabricated spatial filter 50 is positioned in the plane 46 of the Fourier transform pattern. Spatial filter 50 can be fabricated in situ by exposing a recording medium, such as a photographic plate, to light diffracted by all of the dies 14 of wafer 12. This can be accomplished with nonerror-free wafer 12 because the defect information carried by light of relatively low intensity would not expose the photographic plate while Fourier transform information carried by relatively high intensity light exposes the photographic plate. Spatial filter 50 can also be fabricated in accordance with known computer generation techniques.

Spatial filter 50 blocks the spatial frequencies of the error-free Fourier transform of the illuminated dies 14 of wafer 12 but allows the passage of light originating from possible defects in, and light diffracted by other wafer dies proximally located to, such dies. The defect-carrying light rays 52 not blocked by spatial filter 50 strike [an] inverse Fourier transform lens section 54, which is shown schematically as a single lens but includes four lens elements as will be further described below. Inverse Fourier transform lens section 54 performs the inverse Fourier transform on the filtered light pattern of the illuminated wafer dies 14. Lens section 54 is positioned a distance of one focal length away from back focal plane 46 of lens section 34. The elements of lens sections 34 and 54 are aligned along the same optic axis 48, and translation stage 40 moves the wafer dies 14 across the optic axis 48.

A photodetector array 58 is centrally positioned about optic axis 48 in an image plane 60 and receives the image of the defects present in the on-axis portion wafer die 14. Image plane 60 is located in the back focal plane of lens section 54. The magnification of lens section 54 is of an amount that approximately matches the resolution limit of the image to the pixel size of photodetector array 58. In particular, photodetector array 58 has a light sensitive surface 62 whose dimensions are about 10 millimeters $\times$ 10 millimeters within the 30 millimeter diameter image area. A tenfold magnification is, therefore, the proper amount to detect defects in the 3 millimeter diameter area of the on-axis wafer die 14.

To inspect the entire patterned surface of wafer 12, translation stage 40 sequentially moves each portion of the die 14 of wafer 12 to optic axis 48 for illumination by the light emanating from the light source 22. The area of light sensitive surface 62 of the stationary photodetector array 58 limits the amount of light detected to that of a portion of the image corresponding to only the wafer die 14 centered about optic axis 48. The image information corresponding to any portion of illuminated off-axis wafer dies 14 cannot, therefore, reach photodetector array 58. The movement of translation stage 40 is continuous in a stripe-to-stripe raster fashion to implement a time delay integration technique for collecting the defect image information for each die 14 on the patterned surface of wafer 12.

Figure 4:
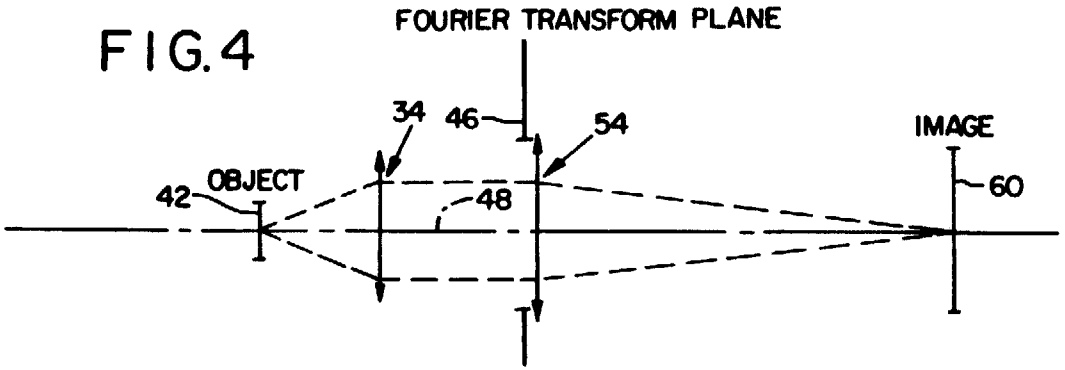
FIG. 4 is a simplified diagram showing the asymmetry of the Fourier transform and inverse Fourier transform lens system incorporated in the defect inspection system of FIG. 1.

The Fourier transform lens section 34 and inverse Fourier transform lens section 54 are designed as part of one optical system 68 and collectively have ten elements as shown in FIG. 4. The design of optical system 68 is complicated by the stringent requirements for two important design parameters, namely, the minimum spot diameter "$d_1$" in Fourier transform plane 46 and minimum spot diameter "$d_2$" in image plane 60. A small minimum spot diameter in Fourier transform plane 46 is required to resolve the bright spots produced in such plane by circuit patterns 16 of the largest expected size. If pattern 16 is of square shape, the required spot diameter $d_1$ satisfies the following expression:

$$d_1 << \lambda f_1/c,$$

where $\lambda$ is the wavelength of light emanating from laser source 22, $f_1$ is the effective focal length of lens section 34, and c is the length of a side of the square pattern 16. A spot diameter $d_1$ of 20 microns can be realized for $c < 300$ microns.

A small minimum spot diameter in image plane 60 determines the smallest possible detectable defect size. The minimum spot diameter $d_2$ is determined by the cooperation of lens sections 34 and 54, and the image magnification "m." A defect of a diameter greater than $d_2/m$ can be measured from the spatial spread of its image. A defect of a diameter less than $d_2/m$, i.e., a subresolution defect, has an image spread that equals $d_2$ but has an image intensity that decreases quadradically with increasing diameter. To detect subresolution defects, inspection system 10 must be designed to achieve substantially lower electronic or optical noise. The design parameter is achievable with the preferred embodiments of inspection system 10 for $d_2=10$ microns, $m=10$, and $d_2/m=1$ micron over the 30 millimeter diameter image field.

Figure 5:
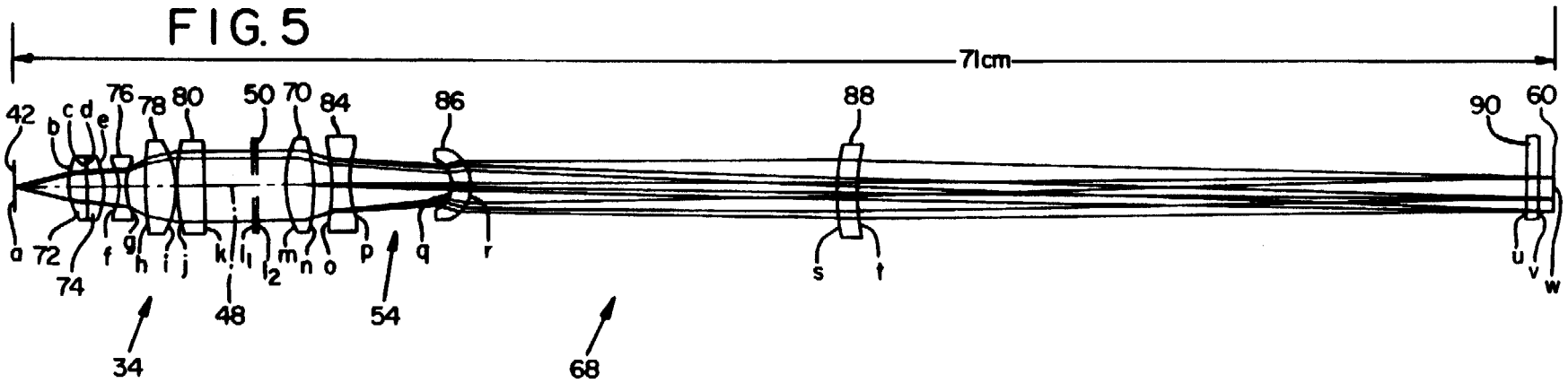
FIG. 5 is a diagram showing the optical elements of the lens system of FIG. 4.

With reference to FIGS. 4 and 5, optical system 68 is a near diffraction-limited optical system that accepts light diffracted into a ±15°-20° telecentric cone, forms the periodic structure of the Fourier transform of the object (i.e., the redundant circuit patterns of a wafer die 14), and produces a detectable image of one-quarter micron or larger diameter defects. The design of lens section 34 is of asymmetric character to form nearly diffraction-limited light pattern at the Fourier transform plane 46. The reason for the asymmetry is that the diffraction angle of optical system 68 is relatively large (±15°-20°) and the 3 millimeter diameter of the surface to be imaged is moderately large. Lens section 54 requires a relatively long focal length $f_2$ to achieve the 10X image magnification. The design of lens section 54 is of asymmetric character and the entrance pupil is positioned closer to the front lens element 72 of lens section 54 to balance residual aberrations introduced by lens section 34 and to minimize the length of optical system 68 and the diameters of the lens elements incorporated in it.

The plane of lens section 54 is positioned nearly in contact with Fourier transform plane 46 to provide a compact signal filtering arrangement. Sufficient space is required between lens section 54 and Fourier transform plane 46 to introduce the illuminating beam through the Fourier transform plane, and to accommodate the mechanical structure that supports spatial filter 50. Optical system 68 is designed so that the image will be an inverted copy of the object with a magnification of $-f_2/f_1$, where $f_2=600$ millimeters, which is the effective focal length of lens section 54, and $f_1=60$ millimeters, which is the effective focal length of lens section 34. Therefore, the magnification "m" equals 10.

Lens section 34 is designed to meet the following two performance requirements. The first and most demanding requirements is that light diffracted into a ±15°-20° telecentric cone from any point on a 3 millimeter diameter object placed at the object or front focal plane 42 is collimated with sufficiently small light ray aberrations to permit the ultimate formation of a near diffraction-limited image with very little geometric distortion. The second requirement is that plane waves propagating through a 20 millimeter object diameter over a range of ±15°-20° have minimum vignetting and produce a light pattern at Fourier transform plane 46 of less than 20 micron resolution spot diameter.

Residual aberrations introduced by lens section 34 into lens section 54 are magnified and are, therefore, nearly impossible to eliminate by compensating aberrations in lens section 54. The design requirements are, therefore, that lens section 34 at Fourier transform plane 46 be 1) isoplanatic (i.e., the aberrations remain constant over a small section of the Fourier transform image field so that the lens is a linear, shift-invariant filter of spatial frequencies), (2) essentially aplanatic (i.e., free from spherical and coma aberrations), and (3) essentially anastigmatic (i.e., having a flat field with no anastigmatism) for incident plane waves over a ±15°-20° diffraction angle and over a 20 millimeter entrance pupil diameter.

To produce a nearly diffraction-limited image at image plane 60, lens section 34 must also produce a plane wave for a point object placed within a 3 millimeter diameter region in the object or front focal plane 42 of the lens. This requires that the chief rays over the ±15°-20° diffraction angle range must be forced to be telecentric (i.e., parallel to optic axis 48) during the design of lens section 34 so that residual aberrations presented to lens section 54 will be very small and compensatible.

The design approach of lens section 34 assumes that it receives light emanating from an infinitely distant object with a ±15°-20° subtense and an entrance pupil placed at front focal plane 42. The Fourier transform light pattern is, therefore, located at the back focal plane 46 of the lens.

In particular, lens section 34 includes five elements positioned along and centered about optic axis 48. Element 72 is a double-convex lens and element 74 is a positive meniscus lens that are positioned close to the entrance pupil of lens system 68 to control spherical aberrations. A double-concave lens 76 controls the field curvature, and double-convex lens 78 and positive meniscus lens 80 are positioned in the converging beam to control astigmatism. To achieve the aberration control driven by the ±15°-20° range of diffraction angles, lens section 34 requires the five elements 72, 74, 76, 78, and 80, which are constructed from glass of a high refractive index.

The design of lens section 54 balances the residual spherical and coma aberrations introduced by lens section 34 when object points are placed at its front focal plane 46 within a 3 millimeter object diameter. A double-convex lens element 70 and a double-concave element 84 are positioned close to Fourier transform plane 46 to cancel the residual spherical aberrations introduced by lens section 34. A negative meniscus lens element 86 cancels the coma aberrations introduced by lens section 34. A positive meniscus lens element 88 of weak positive power distributes the refractive power of lens section 54 so that elements 70, 84, and 86 can introduce the right amount of spherical and coma aberrations to cancel residual aberrations from lens section 34. Lens element 88 also helps correct the astigmatism in the image plane 60. A plano-convex lens element 90 of weak positive power is positioned reasonably close to image plane 60 to control geometric distortion in the image. The positive power of element 90 diminishes, however, the correction of field curvature and astigmatism. The image quality at image plane 60 marginally meets the design objectives because of the limitations imposed by such imbalance of field curvature and astigmatism and the existence of higher order residual spherical aberrations introduced by lens section 34.

Tables I and II summarize the design specifications for and the spacing between adjacent elements of optical system 68. Table I includes the prescription for the elements of lens section 34 and spatial filter 50, and Table II includes the prescription for the elements of lens section 54. The surfaces a-w correspond in general to lettered surfaces in FIG. 5, in which surface "a" corresponds to the object plane 42 and surface "w" corresponds to the image plane 60. Surface $l_1$ and $l_2$ correspond to spatial filter 50. In each instance, the radius and aperture diameter of the surface are given and the shape of each surface is spherical, except for surfaces a, $l_1$, $l_2$, v, and w, which are flat. A positive radius for a surface indicates the center of curvature is to the right in the drawing, and a negative radius indicates the center of curvature is to the left in the drawing (FIG. 5). Dimensions are given in millimeters, and the axial distance to the next surface is measured from left to right in FIG. 5.

TABLE I

| SURFACE | RADIUS OF CURVATURE | AXIAL DISTANCE TO NEXT SURFACE | APERTURE DIAMETER | GLASS TYPE |
|---|---|---|---|---|
| a | INFINITY | 25.4000 | 3.000 | |
| b | 29.4604 | 7.6200 | 16.2210 | SF4 |
| c | −1550.4129 | 0.8196 | 16.4346 | SF4 |
| d | −59.1204 | 6.3500 | 20.0000 | SF4 |
| e | −42.6729 | 7.3181 | 17.3541 | SF4 |
| f | −25.8759 | 3.8100 | 25.4000 | SF8 |
| g | 31.6136 | 9.2731 | 25.4000 | SF8 |
| h | 295.2013 | 12.7000 | 27.1251 | SF4 |
| i | −46.9393 | 1.1064 | 31.8356 | SF4 |
| j | 76.1677 | 12.7000 | 33.6826 | SF4 |
| k | 1792.0762 | 23.0610 | 38.1000 | SF4 |
| $l_1$ | INFINITY | 1.5000 | 38.1000 (10.160 obscured) | K5 |
| $l_2$ | INFINITY | 12.7000 | 38.1000 (10.160 obscured) | K5 |

TABLE II

| SURFACE | RADIUS OF CURVATURE | AXIAL DISTANCE TO NEXT SURFACE | APERTURE DIAMETER | GLASS TYPE |
|---|---|---|---|---|
| m | 44.9835 | 12.7000 | 33.6063 | K5 |
| n | −108.6354 | 8.1484 | 31.5875 | K5 |
| o | −186.5238 | 9.5250 | 31.7500 | SF4 |
| p | 56.7478 | 47.7058 | 31.7500 | SF4 |
| q | −12.2051 | 9.5250 | 22.0000 | SK11 |
| r | −16.9977 | 194.7294 | 27.3846 | SK11 |
| s | 70.7985 | 12.7000 | 37.8796 | SILICA |
| t | 88.1911 | 291.8083 | 38.1000 | SILICA |
| u | 203.8331 | 6.3500 | 33.0126 | BK7 |
| v | INFINITY | 55.9925 | 32.6558 | BK7 |
| w | INFINITY | 0.0000 | 27.8444 | |

Figure 6:
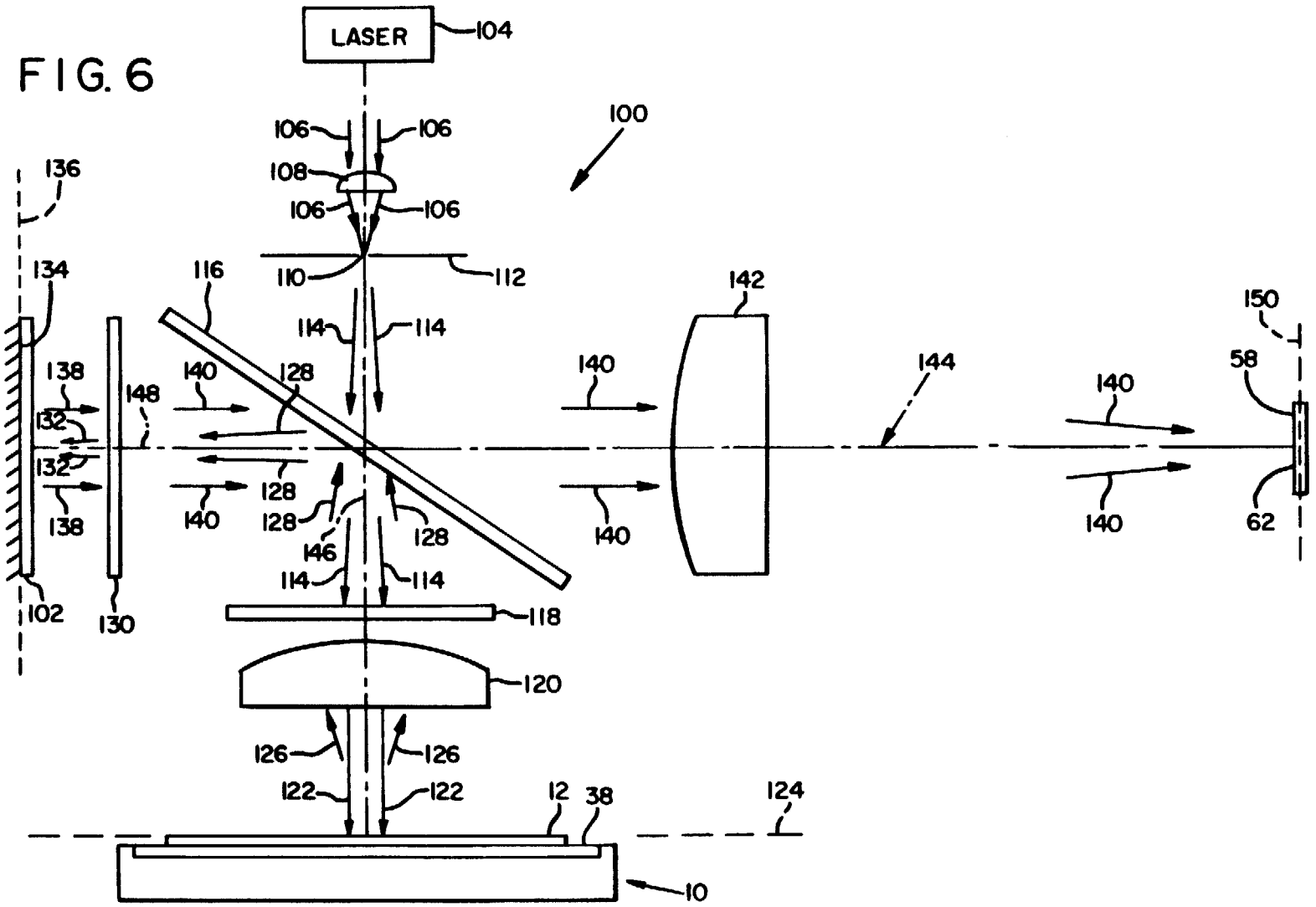
FIG. 6 is a schematic diagram of the optical components of a second preferred embodiment of the defect inspection system of the present invention.

FIG. 6 is a schematic diagram of a second preferred embodiment of an inspection system 100 of the present invention that is designed to detect defects in semiconductor wafers of the kind inspected by the above-described inspection system 10. Inspection system 100 is designed to meet approximately the same performance specifications as those of inspection system 10. Inspection system 100 includes a folded Fourier transform optical system that includes an analytically defined Fourier transform spectral pattern that is inscribed in a liquid crystal layer spatial filter 102. The liquid crystal spatial filter 102 scatters light of the spatial frequencies associated with the regular and periodic structure of, and reflects light of spatial frequencies associated with defects in, the patterned surface of semiconductor wafer 12. That spatial filter 102 reflects light originating from possible defects in wafer 12 dictates the folded Fourier optical configuration of inspection system 100.

With reference to FIG. 6, inspection system 100 includes a laser source 104 that provides a nearly collimated beam of 442.5 nanometer monochromatic light rays 106 that strike a lens 108 that converges the light rays to a point 110 located at the center of the aperture of a pinhole spatial filter 112. The beam of light emitted by laser 104 is linearly polarized in the plane of FIG. 6. The light rays 114 diverging from focal point 110 strike a polarizing beam splitter 116 of the plate type which reflects light rays polarized in the plane perpendicular to the plane of FIG. 6 but transmits light rays polarized in the plane of FIG. 6. A quarter-wave plate 118 receives and imparts circular polarization to the light rays 114 transmitted through beam splitter 116. The circularly polarized light rays 114 exiting quarter-wave plate 118 are confined to a relatively narrow circular beam and propagate toward a Fourier transform lens section 120, which is shown in FIG. 6 as a single element but which is implemented in five lens elements as will be further described below.

The effective center of Fourier transform lens section 120 is positioned a distance of one focal length away from pinhole spatial filter 112 to provide collimated circularly polarized light rays 122 that strike the patterned surface of wafer 12. Wafer 12 is mounted in chuck 38 on translation stage 40, and the collimated light rays 122 illuminate a 20 millimeter diameter of the surface of wafer 12, which is positioned in a front focal or object plane 124 in a manner analogous to that described above for inspection system 10.

Circularly polarized light rays 126 diffracted by the illuminated area of wafer 12 propagate through lens section 120 and quarter-wave plate 118, which develops linearly polarized light rays 128 in a direction perpendicular to the plane of FIG. 6. The light rays 128 reflect off polarizing beam splitter 116 toward a quarter-wave plate 130, which imparts circular polarization to light rays 126. The circularly polarized light rays 132 exiting quarter-wave plane 130 strike the laser absorbing layer 134 of spatial filter 102. The light rays 132 form the Fourier transform pattern of the illuminated wafer surface in the back focal plane 136 of lens section 120.

Spatial filter 102 blocks by absorption the spatial frequencies of the error-free Fourier transform of the illuminated dies 14 of wafer 12 but allows by reflection the passage of light originating from possible defects in such die. Spatial filter 102 differs from spatial filter 50 in two major respects. First, the error-free Fourier transform pattern is inscribed in a liquid crystal layer for spatial filter 102 and in a photographic emulsion deposited on a photographic plate for spatial filter 50. Second, spatial filter 102 is of a reflective type, and spatial filter 50 is of a transmissive type.

The defect-carrying circularly polarized light rays 138 reflected by spatial filter 102 propagate through quarter-wave plate 130, which alters the circular polarization of the light rays and develops linearly polarized light rays 140 whose polarization direction is in the plane of FIG. 6. The light rays 140 propagate through beam splitter 116 and strike an inverse transform Fourier lens section 142, which is shown schematically as a single lens but includes five lens elements as will be further described below. Inverse Fourier transform lens section 142 performs the inverse Fourier transform on the filtered light pattern of the illuminated wafer dies 14. Lens section 142 is positioned a distance of one focal length away from back focal plane 136 of lens section 120. The elements of lens sections 120 and 142 are aligned along or are decentered relative to the same optic axis 144, which is folded into two sections 146 and 148 at the plane of beam splitter 116. Translation stage 40 moves the wafer dies 14 across section 146 of optic axis 144.

Photodetector array 58 is centrally positioned about optic axis 144 in an image plane 150 and receives the image of the defects present on the on-axis position wafer die 14. Image plane 150 is located in the back focal plane of lens section 142. The magnification of lens section 54 is the same as that of, and is determined for the same reasons as those described for, lens section 54 of inspection system 10. The inspection of the entire patterned surface of wafer 12 is accomplished in a manner [analagous] *analogous* to that described below for inspection system 10.

Figure 7:
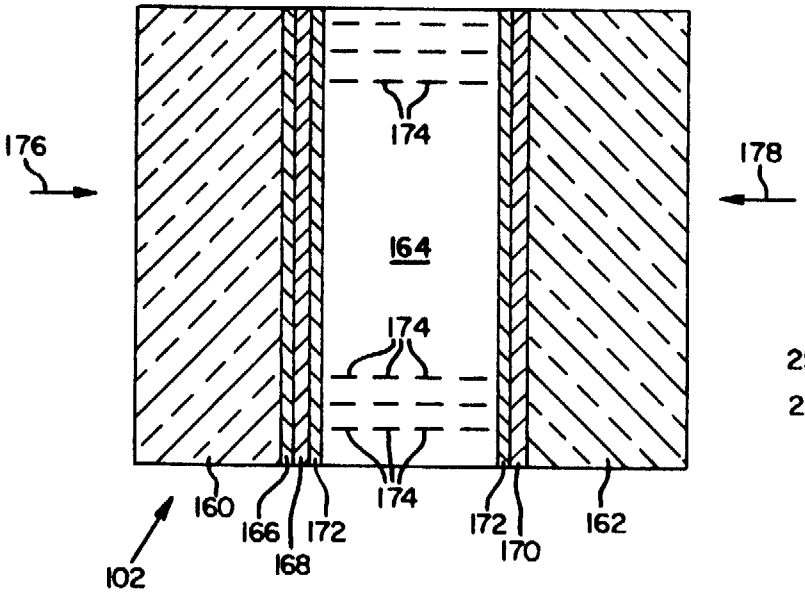
FIG. 7 is a cross sectional view of the spatial filter employed in the defect inspection system of FIG. 6.

FIG. 7 is a cross sectional view of spatial filter 102, which constitutes a laser smectic light valve in which the error-free Fourier transform pattern of wafer 12 is inscribed. The laser smectic light valve of the type employed in the present invention is described in Kahn, Frederic J., "LARGE AREA, ENGINEERING DRAWING QUALITY DISPLAYS USING LASER ADDRESSED SMECTIC LIQUID CRYSTAL LIGHT VALVES," Automation Technology Institute Conference, Montreal, Canada, February 1987.

With reference to FIG. 7, spatial filter 102 comprises a pair of spaced-apart glass substrates 160 and 162 that capture a smectic liquid crystal material 164 between them. A laser absorber layer 166 is applied to the inner surface of glass substrate 160. A reflector electrode 168 is applied to the inner surface of laser absorber layer 166, and a transport electrode 170 is applied to the inner surface of glass substrate 162. Director alignment layers 172 are applied to the inner surface of reflector electrode 168 and the inner surface of transparent electrode 170. The directors 174 of the liquid crystal material 164 contained within the cell have the layered parallel ordering of the smectic phase. The error-free Fourier transform pattern is inscribed in spatial filter 102 in the following way.

A narrowly focused writing laser beam 176 propagates through glass substrate 160 and is focused on laser absorber layer 166, which absorbs the incident laser light and converts it into heat. The heat rapidly diffuses into a localized volume of liquid crystal material 164, raising the temperature of such localized volume by a sufficient amount to heat it above a critical transition temperature. The temperature increase is approximately several degrees Centigrade.

Whenever the temperature of liquid crystal material 164 exceeds the critical transition temperature, the directors 174 thereof no longer have the layered parallel ordering of the smectic phase shown in FIG. 7 but have a random ordering that is characteristic of an ordinary isotropic liquid. Whenever the focused laser beam is extinguished or moved to another writing location, the previously exposed localized volume cools very rapidly back to its ambient operating temperature, the heat diffusing into glass substrates 160 and 162. Glass substrates 160 and 162 are typically 100 to 500 times thicker than liquid crystal material 164, which forms a layer of approximately 13 microns in thickness. Liquid crystal material 164 cools at a rate such that there is insufficient time for directors 174 to reorient to the uniformly ordered smectic configuration. Directors 174 retain their unordered characteristic until they undergo an erasing or editing procedure.

The regions of spatial filter 102 heated by the writing laser beam scatter incident light, and the unheated regions of spatial filter 102 do not scatter light. The written regions scatter incident light propagating in the direction 178 within spatial filter 102 when it is illuminated. The light is scattered so that it is not collected by lens section 142 (FIG. 6). The unwritten regions of spatial filter 102 appear to act like a mirror when the surface of spatial filter 102 is illuminated.

The entire filter pattern can be erased by applying an AC voltage between the transparent electrode 170 on the inner surface of glass substrate 162 and the reflector electrode 168 on laser absorber layer 166. The resultant electric field across liquid crystal material 164 causes directors 174 to align parallel to the applied field and hence normal to the surfaces of glass substrates 160 and 162 to provide the light nonscattering surface.

The error-free Fourier transform can be inscribed into spatial filter 102 by means of a laser-based scanning system that scans laser beam 176 across the surface of glass substrate 160 to illuminate the appropriate areas of laser absorber layer 166 to form the written regions or light scattering spots corresponding to the Fourier transform pattern.

Figure 8:
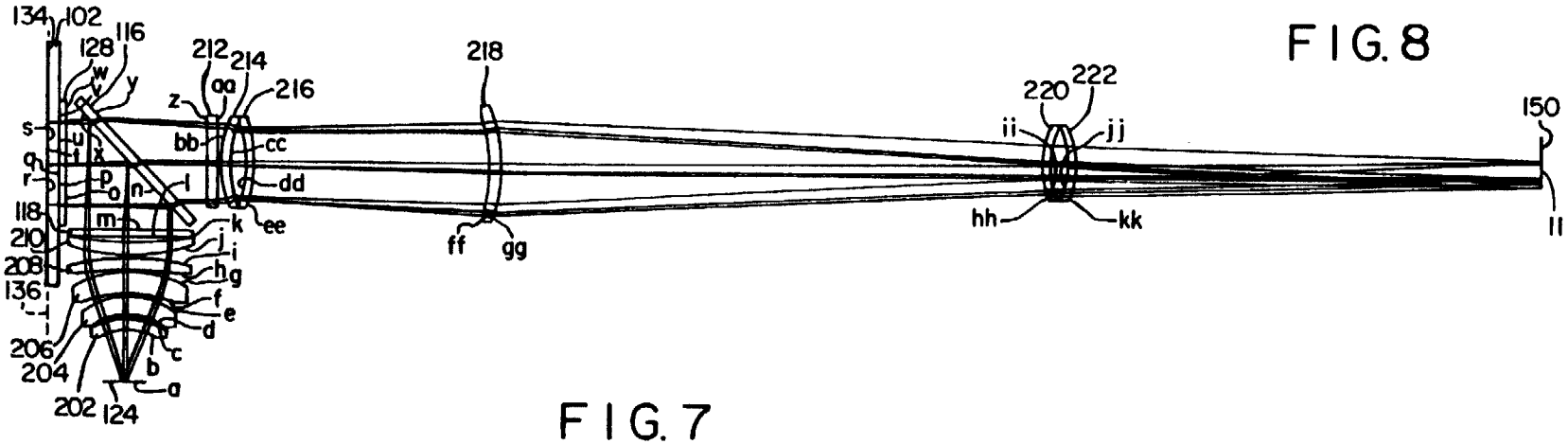
FIG. 8 shows the optical components of the Fourier transform and the inverse Fourier transform lens system incorporated in the defect inspection system of FIG. 6.

The Fourier transform lens section 120 and inverse Fourier transform lens section 142 are designed as part of one optical system 200 and collectively have ten elements as shown in FIG. 8. Lens section 120 is designed to meet the following two performance requirements. The first requirement is that light diffracted into a $\pm 15°$-$20°$ telecentric cone from any point on a 3 millimeter diameter object placed at object or front focal plane 124 be collimated with sufficiently small light ray aberrations to permit the formation of a near diffraction-limited image with very little geometric distortion. The second requirement is that a long back focal length be used to permit folding the system at the plane of beam splitter 116. The design of optical system 200 is complicated by the stringent requirements for the minimum spot diameter "$d_1$" in Fourier transform plane 136 and minimum spot diameter "$d_2$" in image plane 150. The design parameters for spot diameters $d_1$ and $d_2$ and for the image magnification "m" are the same as those described for inspection system 10.

To achieve a back focal length of large dimensions, lens section 120 requires the five elements 202, 204, 206, 208, and 210.

Lens section 120 is of a Berthele eyepiece form because it produces a back focal length of large dimension and accommodates a large relative aperture. Elements 204 and 206 are negative meniscus lenses that provide strong negative power required at the input of the Berthele eyepiece.

Lens section 120 forms the Fourier transform pattern from an incident plane wave and forms in cooperation with lens section 142 an image of tenfold magnification of wafer 12 placed at its front focus 124. This dual function places severe constraints on the design of lens section 120 because the chief rays of the ray fans associated with the diffracted energy that produces the Fourier transform pattern become the rays that construct the axial image point of the magnified image. Under these conditions the magnified image will exhibit very strong spherical aberration whenever the chief rays are not exactly parallel to the optic axis 144 (i.e., telecentric). If the chief rays do not intercept Fourier transform plane 136 in accordance with the sine relationship (i.e., the intercept height equals the sine of the diffraction angle times the focal length of lens section 120), the magnified image would exhibit very strong coma aberration. The magnitude of the coma and spherical aberrations if uncorrected in lens section 120 would be impossible to compensate in lens section 142.

The residual spherical aberration is corrected by a flat plate 212 having a spherical aberration correcting surface positioned downstream of beam splitter 116. Aspheric corrector plate 212 eliminates nearly all of the spherical aberration, but its location and form introduces a modest amount of coma to the magnified image which is removed by lens section 142.

Lens section 142 consists of five elements 214, 216, 218, 220, and 222 that are preferably mounted in a long barrel. Elements 214, 216, and 218 operate as a triplet, which is located immediately after aspheric corrector plate 212. The bending of elements 214, 216, and 218 primarily corrects for coma introduced by aspheric corrector plate 212, and their power distribution and glass types are chosen to control the Petzval field curvature. Elements 220 and 222 correct the residual astigmatism in the system.

Tables III and IV summarize the design specifications for and the spacers between adjacent elements of optical system 220. Table III includes the prescription for the elements of lens section 120, quarter-wave plates 118 and 130, beam splitter 116, and spatial filter 102 and aspheric corrector plate 212; and Table IV includes the prescription for the elements of lens section 142.

TABLE III

| SURFACE | RADIUS OF CURVATURE | AXIAL DISTANCE TO NEXT SURFACE | APERTURE DIAMETER | GLASS TYPE |
|---|---|---|---|---|
| a | INFINITY | 28.5039 | 20.0000 | |
| b | −30.8674 | 4.8260 | 32.7533 | F8 SCHOTT |
| c | −38.4006 | 2.1198 | 36.6157 | F8 SCHOTT |
| d | −28.1656 | 9.5250 | 36.6173 | SF8 SCHOTT |
| e | −38.8061 | 0.5000 | 45.7214 | SF8 SCHOTT |
| f | −72.2881 | 11.9413 | 48.9017 | SF6 SCHOTT |
| g | −55.4938 | 0.5000 | 56.0021 | SF6 SCHOTT |
| h | −635.9805 | 6.9850 | 60.1143 | SF6 SCHOTT |
| i | −103.2759 | 0.5000 | 61.1565 | SF6 SCHOTT |
| j | 88.8919 | 7.2182 | 62.3434 | SF6 SCHOTT |
| k | 210.9940 | 2.8849 | 61.2792 | SF6 SCHOTT |
| l | INFINITY | 3.0000 | 61.1059 | SILICA |
| m | INFINITY | 33.5000 | 60.5615 | SILICA |
| n | INFINITY | −34.0000 | 84.2419 | REFLECTIVE |
| o | INFINITY | −3.0000 | 42.5162 | SILICA |
| p | INFINITY | 0.0000 | 41.9718 | SILICA |
| q | INFINITY | −5.0000 | 41.9718 | SILICA |
| r | INFINITY | 5.0000 | 41.0657 | SILICA |
| s | INFINITY | 0.0000 | 41.0657 | REFLECTIVE |
| t | INFINITY | 5.0000 | 41.0657 | SILICA |
| u | INFINITY | 0.0000 | 41.0657 | SILICA |
| v | INFINITY | 3.0000 | 41.1143 | SILICA |
| w | INFINITY | 34.0000 | 41.1509 | SILICA |
| x | INFINITY | 5.0000 | 59.5915 | BK7 SCHOTT |
| y | INFINITY | 34.3000 | 64.8796 | BK7 SCHOTT |
| z | A(1)* | 5.0000 | 42.4129 | SF1 SCHOTT |
| aa | INFINITY | 1.5000 | 42.6606 | SF1 SCHOTT |

*$(A1) = Ay^4 + By^6 + Cy^8 + Dy^{10}$
where $A = -7.37706 \times 10^{-7}$; $B = -5.25329 \times 10^{-10}$; $C = 5.10552 \times 10^{-13}$; $D = -1.14906 \times 10^{-15}$

TABLE IV

| SURFACE | RADIUS OF CURVATURE | AXIAL DISTANCE TO NEXT SURFACE | APERTURE DIAMETER | GLASS TYPE |
|---|---|---|---|---|
| bb | 44.7640 | 5.0800 | 43.2497 | SF6 SCHOTT |
| cc | 50.2426 | 9.2819 | 41.4749 | SF6 SCHOTT |
| dd | −47.1953 | 3.8100 | 41.4747 | SILICA |
| ee | −80.9227 | 123.9232 | 42.9293 | SILICA |
| ff | −72.3297 | 6.3500 | 57.3855 | SF6 SCHOTT |
| gg | −61.9630 | 311.8775 | 59.4953 | SF6 SCHOTT |
| hh | 43.6306 | 5.0800 | 38.8543 | SILICA |
| ii | 49.5340 | 13.3624 | 37.3900 | SILICA |
| jj | −36.1991 | 5.0800 | 36.7221 | SF6 SCHOTT |
| kk | −42.2545 | 275.6579 | 39.0828 | SF6 SCHOTT |

TABLE IV-continued

| SURFACE | RADIUS OF CURVATURE | AXIAL DISTANCE TO NEXT SURFACE | APERTURE DIAMETER | GLASS TYPE |
|---|---|---|---|---|
| ll | INFINITY | 0.0000 | 30.5109 | |

The surface a-ll correspond in general to lettered sections in FIG. 8, in which surface "a" corresponds to the object plane 124 and surface "ll" corresponds to the image plane 150. Surfaces l-aa correspond to quarter-wave plates 118 and 130, beam splitter 116, spatial filter 102, and aspheric corrector plate 212. Certain surfaces have two letters, one letter representing the surface struck by light propagating toward spatial filter 102 and the other letter representing the surface struck by light reflected by spatial filter 102. In each instance, the radius and aperture diameter of the surface are given and the shape of each surface is spherical, except for surfaces a, l-y, aa, and ll, which are flat, and surface z, which is aspheric. A positive radius for a surface indicates the center of curvature is to the right in the drawing and a negative radius indicates the center of curvature is to the left in the drawing (FIG. 8). Dimensions are given in millimeters, and the axial distance to the next surface is measured in the positive direction from left to right in FIG. 8.

Beam splitter 116 undergoes decentering by 45° rotation in a plane perpendicular to that of FIG. 8. Aspheric corrector plate 212 undergoes decentering by a −2.1642 millimeter displacement downwardly in the vertical direction in FIG. 8. A decenter defines a new coordinate system (displaced and/or rotated) in which subsequent surfaces are defined. Surfaces following a decenter are aligned along the local mechanical axis of the new coordinate system. The new mechanical axis remains in use until changed by another decenter.

Figure 9:
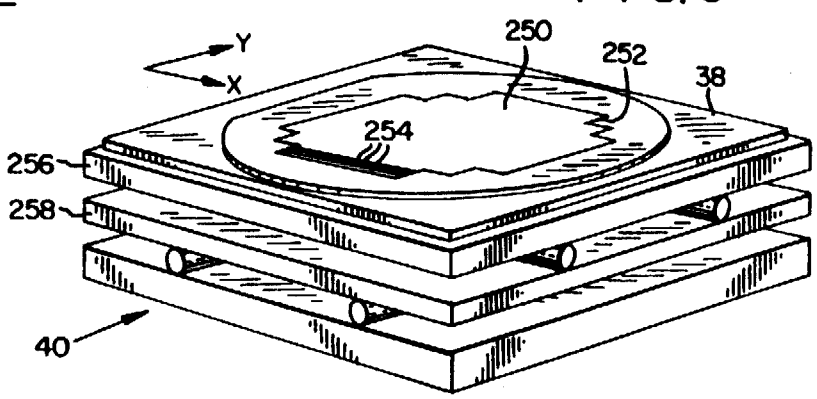
FIG. 9 is an isometric view of the scanning mechanism for detecting the presence and locations of defects in the semiconductor wafer of FIG. 2.

The technique for detecting defects is the same for both of inspection systems 10 and 100; therefore, the following discussion is directed to inspection system 10 only for purposes for illustration. With reference to FIGS. 1 and 9, the presence of defects in wafer 12 is determined by detecting regions of light of intensities which exceed a predetermined threshold amount and which are positioned within an inspection area 250 of a defect image field in image plane 60. Inspection area 250 includes the space contained within the broken outline 252, which is defined by the next adjacent sides of dies 14 to the perimeter of wafer 12 in FIG. 1. Since lens section 54 provides tenfold magnification, the defect image field in image plane 60 has an area that is 100 times that of inspection area 250.

The determination of the presence of defects in wafer 12 is accomplished by partitioning it into stripe regions 254 of 1.0 millimeter in width and moving translation stage 40 in a raster scan fashion so that the 20 millimeter×20 millimeter spot emanating from laser 22 illuminates stripe-by-stripe the entire surface of wafer 12. Since [t] *it* is centrally disposed about optic axis 48 and has a 10 millimeter×10 millimeter light sensitive surface 62, photodetector array 58 detects only the aberration-free inverse Fourier transform light pattern representing a 1.0 millimeter×1.0 millimeter on-axis illuminated region of wafer 12. (The tenfold magnification provided by lens section 54 equalizes the dimensions of the 1.0 millimeter×1.0 millimeter illuminated wafer area and the corresponding 10 millimeter×10 millimeter detected image area.)

Translation stage 40 comprises an X-Y positioning table that is capable of positioning wafer 12 in plane 42 for illumination by the 20 millimeter×20 millimeter beam of light rays 36. A top or Y-stage 256 of translation stage 40 supports chuck 38 and moves wafer 12 along the Y direction in plane 42. A bottom or X-stage 258 of translation stage 40 moves wafer 12 along the X direction in plane 42. One suitable type of X-Y positioning table is a Model 8500 manufactured by Kensington Laboratories, Inc. of Richmond, Calif.

A control circuit (not shown) for translation stage 40 keeps wafer 12 moving at a constant speed as it positions each stripe region for illumination at optic axis 48. Translation stage 40 provides position coordinate information indicating the position of translation stage 40 and the position of defects in the corresponding defect image in image plane 60 relative to a known location on wafer 12. The detection of image defects is performed in accordance with a time delay integration technique, which is described below.

Figures 10A, 10B, 11:
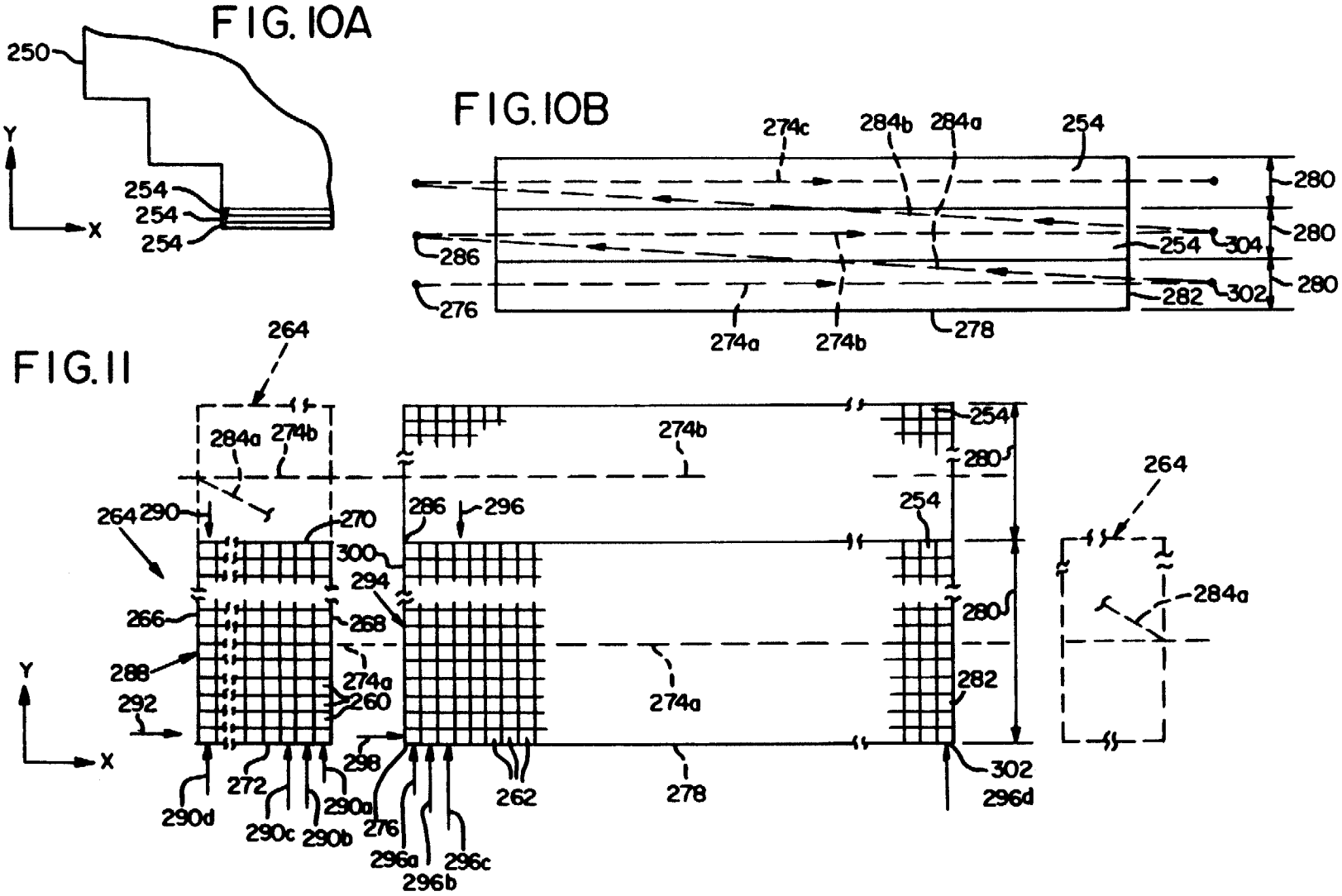
FIG. 10A is an enlarged fragmentary view showing three stripe regions in the lower left-hand corner of the semiconductor wafer of FIG. 9.
FIG. 10B is an enlarged, not-to-scale view of the stripe regions of FIGS. 9 and 10A that shows the raster scan path followed by the scanning mechanism of FIG. 9 relative to a light sensitive detector to detect defect images in a defect image field.
FIG. 11 is a diagram showing an array of pixel elements in the defect image field under tenfold magnification and an array of light detecting elements of a charge-coupled device used in the present invention.

FIGS. 10A and 10B are diagrams of, respectively, the outline of the lower left-hand corner of wafer 12 in FIG. 2 and an enlarged portion thereof to show stripe regions 254 and the raster scan path translation stage 40 travels along time. FIG. 11, which is an enlarged diagram of the portions of the stripe regions of FIG. 10B, shows the one-to-one correspondence between the dimensions of the light detecting elements 260 comprising light sensitive surface 62 of photodetector array 58 and the pixel elements 262 having the same dimensions of light detecting elements 260 because of the tenfold magnification by lens section 54. The photodetector array 58 has 206,336 light detecting elements arranged in 403 rows and 512 columns, as described below.

With reference to FIGS. 10A, 10B, and 11, photodetector array 58 has an optical window 264 through which light passes to be detected by it. Optical window 264 is a rectangle which has sides 266 and 268 that define its length and sides 270 and 272 that define its width. Optical window 264 is fixed generally centrally about optic axis 48. The motion of wafer 12 moves the defect image field, which represents a magnified version of inspection area 250, past optical window 264. For purposes of clarity, however, the following description is presented as though inspection area 250 of wafer 12 moves past control window 264.

In a normal scan operation, translation stage 40 moves wafer 12 past optical window 264 in the X direction so that side 272 of optical window 264 is aligned with the segment 278 of inspection area 250. The movement of wafer 12 past optical window 264 defines along stripe 254 a path segment 274a that has an effective start location 276 and extends to the right in FIGS. 10B and 11. Sides 266 and 268 of optical window 264 are parallel to the Y direction and define the width 280 of a stripe region 254 (three of which are shown in FIG. 9) which represents the portion of inspection area 250 that moves in the X direction past photodetector array 58.

After segment 282 of inspection area 250 moves past side 266 of optical window 264, translation stage 40 moves wafer 12 such that it describes a retrace path segment 284a which extends to the left in FIGS. 10A and 11 to define a start location 286 for the scan of a second adjacent stripe region 254. During retrace, Y-stage 256 moves wafer 12 a distance equal to width 280 (i.e., 100 millimeter) of stripe region 254, and X-stage 258 moves wafer 12 a distance equal to the length of path segment 274a. After retrace, translation stage 40 moves wafer 12 along path segment 274b in the X direction from start location 286 to traverse a second stripe region 254 of width 280.

The above-described scanning and retrace procedure is repeated until the entire inspection area 250 traverses past optic axis 48. There are, however, differences in the lengths of the scan and retrace path segments to accommodate the differences in the dimensions in the X direction of inspection area 250.

With particular reference to FIG. 11, photodetector array 58 of the preferred embodiment is an RCA Model 6220-004 charge-coupled device that includes an array 288 of light detecting elements 260 arranged in rows 290 and columns 292. Array 288 has 403 rows and 512 columns of light detecting elements 260. A row 290 is defined as a group of elements 260 arranged in a line perpendicular to the scan direction (i.e., in the Y direction), and a column 292 is defined as a group of elements 260 arranged in a line parallel to the scan direction (i.e., in the X direction). Each row 290 and each column 292 have lengths of 6.45 millimeters and 10.24 millimeters, respectively. Each light detecting element 260 is 16 microns in length and 20 microns in width. The width of each one of stripe regions 254 is, therefore, equal to the total distance spanned by a row of 403 light detecting elements. Each one of light detecting elements 260 receives through optical window 264 light rays that emanate from the portion of inspection area 250 with which it is aligned and stores in its potential well a quantity of charge or measured energy value that corresponds to the intensity of the light rays incident to it.

Each stripe region 254 of inspection area 250 is divided into an array 294 of pixel elements 262, of which each has the same dimensions as light detecting elements 260 of array 288 by the operation of lens section 54. Pixel elements 262 of array 294 are arranged in rows 296 and columns 298, each row having 403 pixel elements and each column having a number of pixel elements dictated by the length of the stripe region 254. The presence of light in the stripe regions is detected by moving inspection area 250 past optical window 264 of photodetector array 58 along each one of stripe regions 254 and acquiring the energy value corresponding to the intensity of light in each one of pixel elements 262 in accordance with the following procedure.

X-stage 258 commences the scanning process by accelerating wafer 12 from start location 276 toward the left in the X direction until side 268 of optical window 54 is collinear with segment 300 of inspection area 250. X-stage 258 then moves wafer 12 at a nominally constant predetermined speed along stripe region 254.

Whenever light detecting elements 260 in the first row 290a of array 288 align with pixel elements 262 in the first row 296a of array 294, the following events take place. An electrical charge develops in the potential well of each one of light detecting elements 260 in row 290a. The quantity of charge corresponds to the intensity of light present in the pixel element. (The potential wells of light detecting elements 260 have no charge accumulated in them prior to the scan of a stripe region 254.) A row transfer clock signal that is applied to each row 290 of array 288 transfers the charge from each light detecting element 260 in row 290a to the light detecting element in the same column 292 but in the next adjacent or second row 290b. This transfer takes place about the time the light detecting elements and the pixel elements are aligned with each other. (Since X-stage 258 continuously moves wafer 12 along stripe region 254, there is a negligible amount of image degradation that results from aliasing between adjacent rows of the pixel elements.) After the transfer of charge from row 290a to row 290b, there exists no accumulated charge in the potential wells of light detecting elements 260 in row 290a.

Whenever light detecting elements 260 in second row 290b align with pixel elements 262 in the second row 296b of array 294, the following events take place. An electrical charge develops in the potential well of each light detecting element 260 in rows 290a and 290b. The quantity of charge developing in each one of the light detecting elements 260 in row 290b is added to the charge previously transferred to it. The quantity of charge in the light detecting elements 260 in row 290b represents, therefore, two energy values corresponding to the intensity of light present in a pixel element 262 in each column of row 296a of array 294. The row transfer clock signal transfers the charge from each light detecting element 260 in row 290b and row 290a to the light detecting element in the same column 292 but in the next adjacent third row 290c and second row 290b, respectively.

The above-described procedure of (1) acquiring in a light detecting element 260 in a row 290 an energy value corresponding to the intensity of light in a pixel element 262 with which the light detecting element is aligned and (2) transferring the energy value to the light detecting element 260 in the same column 292 but in the next adjacent row 290 with which the pixel element 262 has not previously been aligned is repeated for 255 cycles of the row transfer clock signal.

When 255 such row-to-row transfers have been completed, the light detecting elements in the 256th or last row 290d of array 288 align with the pixel elements 262 in first row 296a of array 294. The 255 previously accumulated energy values for each pixel element 262 in first row 296a are added to the 256th energy value acquired by each light detecting element 260 in last row 290d. Prior to the occurrence of the 256th row transfer clock signal, energy values accumulated in the 512 light detecting elements 260 corresponding to the pixel elements 262 in row 296a are read out serially by a high-speed data transfer clock signal. The accumulated energy values for pixel elements 262 are converted to a digital format and processed by a threshold detector to determine whether the amount of light present in each pixel element 262 indicates the presence of a defect in a corresponding location in wafer 12.

Upon the occurrence of the 256th cycle of the row transfer clock signal, the 255 previously accumulated energy values for each pixel element 262 in second row 296b are added to the 256th energy value acquired by each light detecting element 260 in last row 290d. Prior to the occurrence of the 257th cycle of the row transfer clock signal, the contents of the 512 light detecting elements 260 corresponding to the pixel elements 262 in row 296b are read out and processed as described above.

For each succeeding cycle of the row transfer clock signal, the scan of stripe region 254 continues such that 256 energy values for each pixel element 262 in a row 296 and a column 298 of array 294 are accumulated in the light detecting element 260 in the corresponding column 292 and row 290d of array 288.

There are several general aspects of the accumulation of energy values that characterize the above-described scanning process. First, each one of the light detecting elements 260 in row 290a never accumulates more than one energy value for any one of the pixel elements 262 with which it becomes aligned. Second, the light detecting elements 260 in a row 290 presently aligned with the pixel elements 262 in a particular row 296 always have one more energy value accumulated in them than the light detecting elements 260 in the next adjacent row 290 that was previously aligned with the particular row 296 of pixel elements 262. Third, each one of the light detecting elements 260 in row 290d accumulates 256 energy values corresponding to the light present in the pixel element 262 with which it is aligned.

After segment 282 of inspection area 250 travels completely past side 266 of optical window 264, the scan of a stripe region 254 is completed, and the accumulated energy values of the pixel elements 262 in the last row 296d of array 294 have been read out from the light detecting elements 260 of the last row 290d of array 288. X-stage 258 decelerates wafer 12 to a stop at stop location 302. (In FIG. 11, optical window [54] *264* is shown in phantom for inspection area 250 in this position.) X-stage 258 and Y-stage 256 retrace wafer 12 along path segment 284a to position start location 286 at optical window 264. The potential wells of light detecting elements 260 are cleared during this time in preparation for the scan of the next adjacent stripe region 254. The scan and retrace of the second and succeeding stripe regions 254 proceed as described above.

It will be obvious to those having skill in the art that many changes may be made in the above-described details of the preferred embodiment of the present invention without departing from the underlying principles thereof. For example, a photomask, instead of a semiconductor wafer, can be inspected for defects. [Ispection] *Inspection* systems 10 and 100 would, however, have to be modified to direct the laser light for transmission through the photomask. As a second example, a polarizing beam splitter of the cube type can be substituted for the plate-type beam splitter 116 employed in inspection system 100. A cube type beam splitter would reduce background noise resulting from light reflection but would require a change in the prescription of lens system 200 to reduce spherical aberrations introduced by such a beam splitter. The scope of the present invention should be determined, therefore, only by the following claims.

We claim:

1. In an imaging system that includes first and second lenses positioned along an optic axis, the first lens producing from a specimen a spatial frequency spectrum whose frequency components can be selectively filtered and the second lens producing an image of defects present in the specimen, a method of detecting defects in a specimen that includes an array of normally substantially identical dies, each of the dies having many redundant circuit patterns, comprising:

illuminating plural die circuit patterns;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter to form an image of the defects, the collected spatial frequency components corresponding to a small number of die circuit patterns relative to the number of die circuit patterns in the array of dies and residing in a spatial region intercepting the optic axis; and processing unblocked intra-die spatial frequency components to determine the location and size of a possible defect in [the] *a* die.

2. The method of claim 1 which further comprises changing the position of the specimen relative to the position of the optic axis so that different ones of the die circuit patterns are positioned within the spatial region intercepted by the optic axis, thereby to process the intra-die spatial frequency components of the different ones of the die circuit patterns.

3. The method of claim 1 in which the processing of the unblocked intra-die spatial frequency components is accomplished by positioning a light sensitive detector surface generally centrally about the optic axis, the light sensitive detector surface having an area that is smaller than the surface area of the image of the defects.

4. The method of claim 1 in which the first and second lenses cooperate to receive light diffracted by, and provide an image from the spatial frequency components corresponding to, the illuminated die circuit patterns.

5. The method of claim 4 in which the first lens comprises a first lens section of plural elements and the second lens comprises a second lens section of plural elements, the first and second lens sections forming a near diffraction-limited lens system of asymmetric character.

6. The method of claim 1 in which the illuminating means emits nearly collimated light, the method further comprising:

defining with respect to the specimen plural adjacent stripes, each stripe including a series of adjacent dies;

moving the specimen and the collimated light relative to each other along the length of each stripe to illuminate the die circuit patterns in proximal position to the optic axis; and processing the unblocked intra-die spatial frequency components corresponding to the die circuit patterns in proximal position to the optic axis.

7. The method of claim 6 in which the specimen is movable and the collimated light remains fixed relative to the optic axis.

8. The method of claim 1 in which the relatively transparent and relatively nontransparent portions of the optical filter are developed by computer generation techniques.

9. The method of claim 1 in which the relatively transparent and relatively nontransparent portions of the optical filter are developed by positioning a recording medium in the location of the Fourier transform pattern and exposing the recording medium to light propagating from the specimen.

10. The method of claim 1 in which the collected spatial frequency components correspond to fewer than all of the illuminated die circuit patterns.

11. In an imaging system that includes first and second lenses positioned along an optic axis, the first lens producing from a specimen a spatial frequency spectrum whose frequency components can be selectively filtered and the second lens producing an image of defects present in the specimen, a method of detecting defects in a specimen that includes an array of normally substantially identical dies occupying a first area of the specimen, each of the dies having many redundant circuit patterns, comprising:

illuminating a second area of the specimen, the second area containing die circuit patterns and intercepting the optic axis;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter to form an image of the defects; and processing only unblocked intra-die spatial frequency components to determine the location and size of a possible defect in [the] *a* die.

12. The system of claim 11 in which the size of the first area differs from that of the second area.

13. The system of claim 12 in which the second area is substantially smaller than the first area.

14. The system of claim 12 in which the second area contains more than one die.

15. In an imaging system that includes first and second lenses positioned along an optic axis, the first lens producing from a specimen a spatial frequency spectrum whose frequency components can be selectively filtered and the second lens producing an image of defects present in the specimen, a method of detecting defects in a specimen that includes an array of normally substantially identical dies occupying a first area of the specimen, each of the dies having many redundant circuit patterns, comprising:

illuminating die circuit patterns included within a second area of the specimen;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter to form an image of the defects, the collected spatial frequency components corresponding to fewer than all of the illuminated die circuit patterns; and processing the unblocked intra-die spatial frequency components to determine the location and size of a possible defect in the die.

16. The method of claim 15 in which the second area is substantially smaller than the first area.

17. In an imaging system that includes first and second lenses positioned along an optic axis, the first lens producing from a specimen a spatial frequency spectrum whose frequency components can be selectively filtered and the second lens producing an image of defects present in the specimen, a method of detecting defects in a specimen that includes an array of normally substantially identical dies, each of the dies having many redundant circuit patterns, comprising:

illuminating plural die circuit patterns;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter within a region proximal to the optic axis to form an image of the defects; and processing unblocked intra-die spatial frequency components to determine the location and size of a possible defect in [the] *a* die, the processed spatial frequency components corresponding to a small number of die circuit patterns relative to the number of die circuit patterns in the array of dies and lying in a spatial region intercepting the optic axis.

18. An optical system for detecting defects in a specimen pattern of a type that includes an array of normally essentially identical dies of which each has many redundant circuit patterns and which occupy a first area of the specimen, the system comprising:

illuminating means for illuminating a second area of the specimen, the second area being occupied by plural die circuit patterns;

pattern generating means for generating a light pattern representing substantially the Fourier transform pattern of the illuminated die circuit patterns, the light pattern including intra-die interference pattern information;

optical filter means receiving the light pattern for blocking spatial frequency components thereof, the optical filter means having relatively transparent and relatively nontransparent portions, the relatively nontransparent portion conforming to the Fourier transform of an error-free reference pattern corresponding to the die circuit patterns;

collecting means for collecting the spatial frequency components not blocked by the optical filter means; and processing means for processing only the unblocked intra-die spatial frequency components to determine the location and size of a possible defect in the die.

19. The system of claim 18 in which the illuminating means emits nearly collimated light and which further comprises positioning means for changing the position of the specimen relative to the position of the collimated light so that different ones of the die circuit patterns occupy the second area of the specimen illuminated by the collimated light, thereby to process the intra-die spatial frequency components of the different ones of the die circuit patterns.

20. The system of claim 18 in which the pattern generating means and the collecting means comprises respective first and second lenses positioned along an optic axis that intersects the second area of the specimen illuminated by the illuminating means.

21. The system of claim 18 in which the pattern generating means and the collecting means comprise respective first and second lenses that cooperate to receive light diffracted by, and provide an image from the spatial frequency components corresponding to, the illuminated die circuit patterns.

22. The system of claim 21 in which the first lens comprise a first lens section of plural elements and the second lens comprises a second lens section of plural elements, the first and second lens sections forming a near diffraction-limited lens system of asymmetric character.

23. The system of claim 21 in which the first lens comprises a first lens section of plural elements and the second lens comprises a second lens section of plural elements, the first lens section forming the Fourier transform pattern and cooperating with the second lens section to provide a magnified image of the defects in the illuminated die circuit patterns.

24. The system of claim 18 in which the pattern generating means and the collecting means comprise a folded Fourier transform optical system that receives light diffracted by, and provides an image from the spatial frequency components corresponding to, the illuminated die circuit patterns.

25. The system of claim 24 in which the specimen comprises a semiconductor wafer.

26. The system of claim 24 in which the optical filter means comprises a liquid crystal layer.

27. The system of claim 26 in which the relatively nontransparent portion of the liquid crystal layer scatters light of the spatial frequencies incident to it.

28. The system of claim 18 in which the optical filter means comprises a liquid crystal layer.

29. The system of claim 28 in which the relatively nontransparent portion of the liquid crystal layer scatters light of the spatial frequencies incident to it.

30. The system of claim 18 in which the optical filter means comprises exposed light sensitive material.

31. The system of claim 18 in which the optical filter means comprises a lens assembly that has an aperture of at least $\pm 15°$.

32. The system of claim 18 in which the Fourier transform light pattern represents the Fourier transform image.

33. The system of claim 18 in which the specimen comprises a semiconductor wafer.

34. The system of claim 18 in which the second area is substantially smaller than the first area.

35. The system of claim 18 in which the illuminating means emits nearly collimated light and the processing means comprises a light sensitive detector having a light sensitive surface positioned generally centrally about the optic axis[,] : the light detector including plural light detecting elements arranged in a first array of rows and columns and defining in the light pattern plural adjacent stripe regions each of which includes plural pixel elements arranged in a second array of rows and columns, and each light detecting element being operable to provide a measured energy value corresponding to the amount of light present in any one of the pixel elements, and the system further comprising:

positioning means for positioning the specimen relative to the collimated light to scan the light detecting means along a stripe region of the light pattern so that in succession each light detecting element in one column of the first array traverses and acquires an energy value corresponding to the amount of light present in a pixel element in one column of the second array;

accumulating means to accumulate a total energy value proportional to the sum of the energy values acquired for the pixel element by all of the light detecting elements in the one column of the first array; and means to determine from the total energy value whether the amount of light in the pixel element represents a defect in the specimen subject.

36. The system of claim 35 in which the light detector comprises a charge-coupled device.

37. The system of claim 35 in which the collimated light remains stationary and the positioning means scans each one of the stripe regions across the light sensitive surface in a serial manner.

38. The system of claim 37 in which the positioning means continuously moves each stripe region across the collimated light.

39. The system of claim 35 in which the first array has a first row and N total number of rows and which further comprises position-detecting means for detecting the position of the first array relative to the stripe region, the position-detecting means cooperating with the accumulating means so that each one of the light detecting elements in the first row of the one column never accumulates more than one energy value for any one of the pixel elements of the second array with which it becomes aligned, and each one of the light detecting elements in the Nth row of the one column has accumulated N number of energy values for any one of the pixel elements with which it becomes aligned.

*40. In an imaging system that includes first and second lenses positioned along an optic axis, the first lens producing from a specimen a spatial frequency spectrum whose frequency components can be selectively filtered and the second lens producing an image of defects present in the specimen, a method of detecting nonperiodic defects in a specimen that includes one or more dies having many redundant circuit patterns, comprising:*

*illuminating plural die circuit patterns;*

*generating a light pattern representing substantially the Fourier transform pattern of the illuminated die circuit patterns, the light pattern including intra-die interference pattern information;*

*positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;*

*collecting spatial frequency components not blocked by the optical filter to form an image of the defects, the collected spatial frequency components corresponding to a small number of die circuit patterns relative to the*

*number of illuminated die circuit patterns and residing in a spatial region intercepting the optic axis; and*

*processing unblocked intra-die circuit pattern spatial frequency components to determine the presence of a possible nonperiodic defect in a die.*

*41. The method of claim 40 which further comprises changing the position of the specimen relative to the position of the optic axis so that different ones of the die circuit patterns are positioned within the spatial region intercepted by the optic axis, thereby to process the intra-die spatial frequency components of the different ones of the die circuit patterns.*

*42. The method of claim 40 in which the processing of the unblocked intra-die spatial frequency components is accomplished by positioning a light sensitive detector surface generally centrally about the optic axis, the light sensitive detector surface having an area that is smaller than the surface area of the image of the defects.*

*43. The method of claim 40 in which the first and second lenses cooperate to receive light diffracted by, and provide an image from the spatial frequency components corresponding to, the illuminated die circuit patterns.*

*44. The method of claim 40 in which the illuminating means emits substantially collimated light, the method further comprising:*

*defining with respect to the specimen adjacent stripes for scanning through many redundant die circuit patterns;*

*moving the specimen and the collimated light relative to each other along the length of each stripe to illuminate die circuit patterns in proximal position to the optic axis; and*

*processing the unblocked intra-die spatial frequency components corresponding to the die circuit patterns in proximal position to the optic axis.*

*45. The method of claim 44 in which the stripe for scanning includes more than one area of redundant die circuit patterns.*

*46. The method of claim 44 in which the stripe for scanning traverses through one or more dies.*

*47. An optical system for detecting nonperiodic defects in a specimen pattern of a type that includes one or more dies having many redundant circuit patterns occupying a first area of the specimen, the system comprising:*

*illuminating means for illuminating a second area of the specimen, the second area being occupied by plural redundant die circuit patterns;*

*pattern generating means for generating a light pattern representing substantially the Fourier transform pattern of the illuminated die circuit patterns, the light pattern including intra-die interference pattern information;*

*optical filter means receiving the light pattern for blocking spatial frequency components thereof, the optical filter means having relatively transparent and relatively nontransparent portions, the relatively nontransparent portion conforming to the Fourier transform of an error-free reference pattern corresponding to the die circuit patterns;*

*collecting means for collecting the spatial frequency components not blocked by the optical filter means; and*

*processing means for processing the unblocked intra-die spatial frequency components to determine the presence of a possible nonperiodic defect in a die.*

*48. The system of claim 47 in which the illuminating means emits substantially collimated light and in which the collecting means collects spatial frequency components residing in a spatial region intercepting the optic axis, the spatial frequency components corresponding to a smaller number of die circuit patterns relative to the number of illuminated die circuit patterns and being in proximal position to the optic axis.*

*49. The system of claim 47 in which further comprises positioning means for changing the position of the specimen so that different ones of the die circuit patterns are positioned within the second area, thereby to process the intra-die spatial frequency components of the different ones of the die circuit patterns.*

*50. The system of claim 47 in which the collecting means collects spatial frequency components corresponding to fewer than all of the illuminated die circuit patterns.*

*51. The system of claim 47 in which the illuminating means emits substantially collimated light and in which the pattern generating means and the collecting means comprise respective first and second lenses that cooperate to receive light diffracted by, and provide an image from the spatial frequency components residing in a spatial region intercepting the optic axis and corresponding to, a smaller number of die circuit patterns relative to the number of illuminated die circuit patterns and positioned proximally to the optic axis, the system further comprising:*

*positioning means for changing the position of the specimen relative to the position of the collimated light to scan the specimen in stripes so that different ones of the die circuit patterns serially occupy the second area.*

*52. The system of claim 51 in which the positioning means scans a stripe that traverses one or more dies including one or more areas having many redundant die circuit patterns.*

*53. The system of claim 51 in which the first lens comprises a first lens section of plural elements and the second lens comprises a second lens section of plural elements, the first and second lens sections forming a near diffraction-limited lens system of asymmetric character.*

*54. The system of claim 51 in which the first lens comprises a first lens section of plural elements and the second lens comprises a second lens section of plural elements, the first lens section forming the Fourier transform pattern and cooperating with the second lens section to provide a magnified image of the defects in the illuminated die circuit patterns.*

*55. In an imaging system that includes first and second lenses positioned along an optic axis, the first lens producing from a specimen a spatial frequency spectrum whose frequency components can be selectively filtered and the second lens producing an image of defects present in the specimen, a method of detecting nonperiodic defects in a specimen that includes one or more dies having many redundant die circuit patterns, comprising:*

*illuminating a small number of die circuit patterns relative to the number of die circuit patterns in the specimen;*

*generating a light pattern representing substantially the Fourier transform pattern of the illuminated die circuit patterns, the light pattern including intra-die interference pattern information;*

*positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;*

*collecting spatial frequency components not blocked by the optical filter to form an image of the defects, the*

*collected spatial frequency components residing in a spatial region intercepting the optic axis and corresponding to a small number of die circuit patterns relative to the number of illuminated die circuit patterns and being in proximal position to the optic axis; and*

*processing the unblocked intra-die spatial frequency components to determine the presence of a possible nonperiodic defect.*

*56. The method of claim 55 which further comprises changing the position of the specimen relative to the position of the optic axis so that spatial frequency components of different ones of the die circuit patterns are collected within the spatial region intercepted by the optic axis, thereby to process the intra-die spatial frequency components of the different ones of the die circuit patterns.*

*57. The method of claim 55 in which the illuminating means emits nearly collimated light, the method further comprising:*

*defining with respect to the specimen adjacent stripes for scanning through many redundant die circuit patterns;*

*moving the specimen and the collimated light relative to each other along the length of each stripe to illuminate the circuit patterns; and*

*processing the unblocked intra-die frequency components corresponding to the circuit patterns in proximal position to the optic axis.*

*58. The method of claim 57 in which the stripe for scanning traverses through one or more dies.*

* * * * *

US001033956A

REEXAMINATION CERTIFICATE (2309th)

United States Patent [19]

[11] B1 Re. 33,956

Lin et al.

[45] Certificate Issued Jun. 7, 1994

[54] INSPECTION SYSTEM FOR ARRAY OF MICROCIRCUIT DIES HAVING REDUNDANT CIRCUIT PATTERNS

[75] Inventors: Lawrence H. Lin, Alamo; Daniel L. Cavan, Woodside; Robert B. Howe, San Jose, all of Calif.

[73] Assignee: Optical Specialties, Inc., Fremont, Calif.

Reexamination Request:
No. 90/003,180, Aug. 30, 1993

Reexamination Certificate for:

| | |
|---|---|
| Patent No.: | **Re. 33,956** |
| Issued: | **Jun. 9, 1992** |
| Appl. No.: | **613,208** |
| Filed: | **Nov. 14, 1990** |

Related U.S. Patent Documents

Reissue of:

| | |
|---|---|
| [64] Patent No.: | **4,806,774** |
| Issued: | **Feb. 21, 1989** |
| Appl. No.: | **60,090** |
| Filed: | **Jun. 8, 1987** |

[51] Int. Cl.[5] ..... G02B 27/42

[52] U.S. Cl. ..... 250/550; 250/572; 382/31; 356/237; 356/354

[58] Field of Search ..... 250/562, 563, 550, 572, 250/548; 356/392, 394, 354, 237; 382/31

[56] References Cited

U.S. PATENT DOCUMENTS

| | | | |
|---|---|---|---|
| 3,614,232 | 10/1971 | Mathisen | 356/71 |
| 3,658,420 | 4/1972 | Axelrod | 356/71 |
| 4,000,949 | 1/1977 | Watkins | 356/165 |
| 4,330,775 | 5/1982 | Iwamoto et al. | 340/146.3 P |
| 4,516,833 | 5/1985 | Fusek | 350/162.12 |

FOREIGN PATENT DOCUMENTS

| | | | |
|---|---|---|---|
| 2384407 | 3/1977 | France | H04N 7/02 |
| 153151 | 9/1984 | Japan | G01N 21/88 |

OTHER PUBLICATIONS

Axelrod, N. N., Intensity Spatial Filtering Applied to Defect Detection in Integrated Circuits, Proc. IEEE, Apr. 1972, pp. 447–448.

*Primary Examiner*—Edward Westin

[57] ABSTRACT

An inspection system (10, 100) employs a Fourier transform lens (34, 120) and an inverse Fourier transform lens (54, 142) positioned along an optic axis (48, 144) to produce from an illuminated area of a patterned specimen wafer (12) a spatial frequency spectrum whose frequency components can be selectively filtered to produce an image pattern of defects in the illuminated area of the wafer. Depending on the optical component configuration of the inspection system, the filtering can be accomplished by a spatial filter of either the transmissive (50) or reflective (102) type. The lenses collect light diffracted by a wafer die (14) aligned with the optic axis and light diffracted by other wafer dies proximately located to such die. The inspection system is useful for inspecting only dies having many redundant circuit patterns. The filtered image strikes the surface of a two-dimensional photodetector array (58) which detects the presence of light corresponding to defects in only the illuminated on-axis wafer die. Inspection of all possible defects in the portions of the wafer surface having many redundant circuit patterns is accomplished by mounting the wafer onto a two-dimensional translation stage and moving the stage (40) so that the illuminated area continuously scans across the wafer surface from die to die until the desired portions of the wafer surface have been illuminated. The use of a time delay integration technique permits continuous stage movement and inspection of the wafer surface in a raster scan fashion.

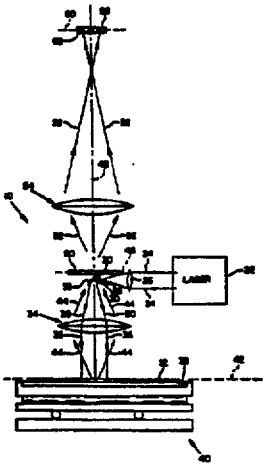

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-39 is confirmed.

Claims 40, 47, 55 are determined to be patentable as amended.

Claims 41-46, 48-54, 56, dependent on an amended claim, are determined to be patentable.

1. In an imaging system that includes first and second lenses positioned along an optic axis, the first lens producing from a specimen a spatial frequency spectrum whose frequency components can be selectively filtered and the second lens producing an image of defects present in the specimen, a method of detecting defects in a specimen that includes an array of normally substantially identical dies, each of the dies having many redundant circuit patterns, comprising:

illuminating plural die circuit patterns;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter to form an image of the defects, the collected spatial frequency components corresponding to a small number of die circuit patterns relative to the number of die circuit patterns in the array of dies and residing in a spatial region intercepting the optic axis; and processing unblocked intra-die frequency components to determine the location and size of a possible defect in [the] *a* die.

40. In an imaging system that includes first and second lenses positioned along an optic axis, the first lens producing from a specimen a spatial frequency spectrum whose frequency components can be selectively filtered and the second lens producing an image of defects present in the specimen, a method of detecting nonperiodic defects in a specimen that includes one or more dies *each* having many redundant circuit patterns, comprising:

illuminating plural die circuit patterns;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter to form an image of the defects, the collected spatial frequency components corresponding to a small number of die circuit patterns relative to the number of illuminated die circuit patterns and residing in a spatial region intercepting the optic axis; and processing unblocked intra-die circuit pattern spatial frequency components to determine the presence of a possible nonperiodic defect in a die.

47. An optical system for detecting nonperiodic defects in a specimen pattern of a type that includes one or more dies *each* having many redundant circuit patterns occupying a first area of the specimen, the system comprising:

illuminating means for illuminating a second area of the specimen, the second area being occupied by plural redundant die circuit patterns;

pattern generating means for generating a light pattern representing substantially the Fourier transform pattern of the illuminated die circuit patterns, the light pattern including intra-die interference pattern information;

optical filter means receiving the light pattern for blocking spatial frequency components thereof, the optical filter means having relatively transparent and relatively nontransparent portions, the relatively nontransparent portion conforming to the Fourier transform of an error-free reference pattern corresponding to the die circuit patterns;

collecting means for collecting the spatial frequency components not blocked by the optical filter means; and processing means for processing the unblocked intra-die spatial frequency components to determine the presence of a possible nonperiodic defect in a die.

55. In an imaging system that includes first and second lenses positioned along an optic axis, the first lens producing from a specimen a spatial frequency spectrum whose frequency components can be selectively filtered and the second lens producing an image of defects present in the specimen, a method of detecting nonperiodic defects in a specimen that includes one or more dies *each* having many redundant die circuit patterns, comprising:

illuminating a small number of die circuit patterns relative to the number of die circuit patterns in the specimen;

generating a light pattern representing substantially the Fourier transform pattern of the illuminated die circuit patterns, the light pattern including intra-die interference pattern information;

positioning an optical filter to receive the light pattern and to block spatial frequency components thereof, the optical filter having relatively transparent and relatively nontransparent portions, the relatively nontransparent portion conforming to the Fourier transform pattern of an error-free reference pattern corresponding to the die circuit patterns;

collecting spatial frequency components not blocked by the optical filter to form an image of the defects, the collected spatial frequency components residing in a spatial region intercepting the optic axis and corresponding to a small number of die circuit patterns relative to the number of illuminated die circuit patterns and being in proximal position to the optical axis; and processing the unblocked intra-die spatial frequency components to determine the presence of a possible nonperiodic defect *in a die.*

* * * * *